(12) United States Patent
Aung et al.

(10) Patent No.: US 11,076,788 B2
(45) Date of Patent: Aug. 3, 2021

(54) METHOD AND APPARATUS FOR DERIVING A MENTAL STATE OF A SUBJECT

(71) Applicant: Nitto Denko Corporation, Osaka (JP)

(72) Inventors: Aye Aung, Singapore (SG); Kittipong Kasamsook, Singapore (SG); Visit Thaveeprungsriporn, Singapore (SG); Pimporn Muaynoi, Singapore (SG)

(73) Assignee: Nitto Denko Corporation

(*) Notice: Subject to any disclaimer, the term of this patent is extended or adjusted under 35 U.S.C. 154(b) by 210 days.

(21) Appl. No.: 15/537,967

(22) PCT Filed: Dec. 23, 2015

(86) PCT No.: PCT/SG2015/050500
§ 371 (c)(1),
(2) Date: Jun. 20, 2017

(87) PCT Pub. No.: WO2016/108754
PCT Pub. Date: Jul. 7, 2016

(65) Prior Publication Data
US 2017/0340257 A1    Nov. 30, 2017

(30) Foreign Application Priority Data

Dec. 30, 2014    (WO) ................ PCT/SG2014/000622

(51) Int. Cl.
*A61B 5/16* (2006.01)
*A61B 5/0205* (2006.01)
(Continued)

(52) U.S. Cl.
CPC .............. *A61B 5/165* (2013.01); *A61B 5/021* (2013.01); *A61B 5/024* (2013.01); *A61B 5/0205* (2013.01);
(Continued)

(58) Field of Classification Search
CPC ....... A61B 5/165; A61B 5/167; A61B 5/0205; A61B 5/021; A61B 5/024; A61B 5/02405;
(Continued)

(56) References Cited

U.S. PATENT DOCUMENTS 8,700,009 B2    4/2014  Quy
2003/0078505 A1    4/2003  Kim et al.
(Continued)

FOREIGN PATENT DOCUMENTS

CN    101708121 A    5/2010
CN    102551699 A    7/2012
(Continued)

OTHER PUBLICATIONS

Takai, Noriyasu "Effect of psychological stress on the salivary cortisol and amylase levels in healthy young adults" Archives of Oral Biology (2004) vol. 49, 963-968 (Year: 2004).*
(Continued)

*Primary Examiner* — Matthew Kremer
*Assistant Examiner* — Avery M Foley
(74) *Attorney, Agent, or Firm* — Lerner, David, Littenberg, Krumholz & Mentlik, LLP

(57) ABSTRACT

A method (1500) for deriving a mental state of a subject is disclosed. The method comprises receiving (1502) a bio-signal from the subject; calculating respective statistical variations of at least two physiological parameters derived from the bio-signal; determining (1504) an arousal level of the subject based on the calculated statistical variations of the at least two physiological parameters; deriving a time-domain heart rate variability signal from the bio-signal for calculating at least two heart rate variability parameters; determining (1506) a valence level of the subject based on the at least two heart rate variability parameters; and deriv-
(Continued)

ing (1508) the mental state from the arousal level and valence level. A related apparatus is also disclosed.

10 Claims, 13 Drawing Sheets

(51) Int. Cl.
   *A61B 5/021*    (2006.01)
   *A61B 5/024*    (2006.01)
   *A61B 5/08*     (2006.01)
   *A61B 5/00*     (2006.01)
   *A61B 5/145*    (2006.01)

(52) U.S. Cl.
   CPC ........ *A61B 5/02405* (2013.01); *A61B 5/0816* (2013.01); *A61B 5/16* (2013.01); *A61B 5/7239* (2013.01); *A61B 5/14507* (2013.01)

(58) Field of Classification Search
   CPC ....... A61B 5/0816; A61B 5/16; A61B 5/7239; A61B 5/14507
   See application file for complete search history.

(56) References Cited

U.S. PATENT DOCUMENTS

| | | |
|---|---|---|
| 2006/0004266 A1 | 1/2006 | Shirai et al. |
| 2006/0155206 A1* | 7/2006 | Lynn ................. A61B 7/003 600/529 |
| 2008/0214903 A1 | 9/2008 | Orbach |
| 2011/0300847 A1 | 12/2011 | Quy |
| 2011/0301433 A1 | 12/2011 | Sadowsky et al. |
| 2013/0046189 A1* | 2/2013 | Kirchner ............. A61B 5/0215 600/484 |
| 2013/0245396 A1 | 9/2013 | Berman et al. |
| 2014/0046189 A1 | 2/2014 | Jain et al. |
| 2014/0221866 A1 | 8/2014 | Quy |
| 2015/0112606 A1* | 4/2015 | He .................... A61B 5/02427 702/19 |
| 2015/0245777 A1* | 9/2015 | Della Torre ............. A61B 5/11 600/301 |

FOREIGN PATENT DOCUMENTS

| | | |
|---|---|---|
| JP | 2002112969 A | 4/2002 |
| JP | 2006015046 A | 1/2006 |
| JP | 2008532587 A | 8/2008 |
| JP | 2013027570 A | 2/2013 |
| JP | 2013537435 A | 10/2013 |
| JP | 2014036847 A | 2/2014 |
| WO | 2014031082 A1 | 2/2014 |
| WO | 2014063160 A1 | 4/2014 |

OTHER PUBLICATIONS

Trapp, Michael "Impact of Mental and Physical Stress on Blood Pressure and Pulse Pressure under Normobaric versus Hypoxic Conditions" PLoS One, May 2014; vol. 9, Issue 5; e89005 (Year: 2014).*
Bridges, P.K. et al. "A taxonomic study of physiological responses to a psychological stress" J. Neurol. Neurosurg. Psychiat., 1970, 33, 180-187 (Year: 1970).*
Extended European Search Report including Written Opinion for EP 15875799.7 dated Oct. 18, 2018.
International Search Report for Application No. PCT/SG2015/050500 dated Mar. 7, 2016.
Chinese Search Report for Application No. CN 201580076908.3 dated Nov. 14, 2019, 4 pages.

* cited by examiner

800

| Feature | Normal condition | Stress Condition | P Value |
|---|---|---|---|
| | Mean | Mean | |
| PP | 12.32 | 35.67 | 1.81E-08 |
| SDPP | 2.86 | 13.05 | 1.05E-15 |
| SDHR | 4.14 | 5.94 | 6.20E-08 |
| SDNN | 59.12 | 57.37 | 0.578254 |
| pNN50 | 36.39 | 18.50 | 4.13E-11 |
| HRV Corr | 48.45 | 47.04 | 0.161235 |
| Kurtosis | 16.45 | 14.66 | 0.202784 |

FIG. 8

| Frequency Range | Interpretation |
|---|---|
| Low Frequency (LF: 0.04-0.15 Hz) | Reflect combination of Sympathetic Nervous System (SNS) and Parasympathetic NS (PNS) influence |
| High Frequency (HF: 0.15 - 0.4 Hz) | Under normal circumstances reflect Parasympathetic activity |
| LF/HF | Reflect balance of SNS/PNS |

(a)

(b)

1400

If user LF/HF > X, Kurtosis < A & HRV Coherence < B, Valence Level = Normal

METHOD AND APPARATUS FOR DERIVING A MENTAL STATE OF A SUBJECT

CROSS REFERENCE TO RELATED APPLICATIONS

The present application is a national phase entry under 35 U.S.C. § 371 of International Application No. PCT/SG2015/050500, filed Dec. 23, 2015, published in English, which claims priority to International Application No. PCT/SG2014/000622, filed Dec. 30, 2014, published in English.

FIELD

The present invention relates to a method and apparatus for deriving a mental state of a subject.

BACKGROUND

Emotional arousal is a human body's natural response to the ever changing conditions around us. In the presence of stress arousal, the human body instinctively produces "flight or fight" stress (reaction) hormones such as adrenaline or cortisol. Secretion of the stress hormones into the blood stream results in characteristic physiological changes to the heart rate, blood pressure, breathing as well as muscular functioning. These changes help an individual stay focused, energetic and alert so that he/she may react and cope with the situations correctly and efficiently.

Although stress is considered essential and beneficial for daily performance, chronic exposure to high levels of stress hormones is also known to increase risk of hypertension, immune-suppression, indigestion, depression, anxiety disorders, loss of libido, headaches, loss of memory, lack of concentration, learning difficulties, insomnia or the like.

FIG. 1 is a graph 100 showing one example of an empirical relationship between arousal level and performance, which is known as the Yerkes-Dodson curve, whereby the Yerkes-Dodson law dictates that performance tends to increase with increasing levels of arousal until a certain point and from thereon, decreases instead. Research has also found that different tasks require different levels of arousal for optimal performance and thus a shape of the Yerkes-Dodson curve may be highly variable. For intellectually demanding tasks, a lower level of arousal is required to enable concentration, whereas for tasks that demand stamina or persistence, a higher level of arousal is instead required to facilitate motivation. A further example is shown in a graph 200 in FIG. 2. For simple or well-learned tasks, the relationship between arousal level and performance may be considered linear with improvements in performance as the arousal level increases. But for complex, unfamiliar or difficult tasks, the relationship between arousal level and performance is reversed, whereby the performance decreases as arousal level increases.

Depending how an individual reacts towards and perceives a situation he/she encounters, stress is typically experienced in two different forms. A positive form of stress, also known as eustress, motivates and fuels the individual to achieve his/her peak performance. Individuals experiencing this positive stress often describe themselves as being "pumped up" or "being psyched". It is also believed that there is an ideal amount of eustress that an individual needs to experience in order to work at his/her optimum level. Too little eustress and an individual may get bored, while too much eustress may however lead the individual to act recklessly, make poor decisions, and be worn down (both physically and mentally). On the other hand, negative stress or distress, is often associated with an individual experiencing negative emotions such as anxiety or worry. This kind of negative stress undesirably reduces performance and causes mental and physical drawbacks as described above.

It is to be appreciated that a healthy heart typically has a natural beat-to-beat variation in rate, known as Heart Rate Variability (HRV). Patterns and rhythms within this variability are important to health and general well-being. Research has shown that when an individual shifts into a different emotional state, his/her heart rhythms changes immediately. Specifically, negative emotions (or negative valence), such as anxiety and frustration, are associated with a disordered and chaotic variation. On the other hand, positive emotions (or positive valence), such as calmness and tranquillity, tend to show an ordered rhythm synchronized with breathing which is also known as HRV coherence. Hence, an individual who is able to control his/her HRV coherence may subsequently see improved cognitive performance and emotional well-being.

Indeed, it is thus important for an individual to be aware of his/her emotional state so that necessary actions may be taken to maintain his/her overall physical and mental well-being.

Presently, common methods employed by psychologists for assessing emotional well-being typically involve interviews, questionnaires as well as participant self-scoring. Results from such tests often however suffer from judgemental errors from both the observers and participants. Other methods of assessment may include salivary cortisol testing, which can be rather troublesome and time consuming, even though it is fairly accurate in detecting stress. It is thus not feasible for an individual to continuously monitor his/her emotional levels using conventional solutions, especially for over an extended period of time.

One object of the present invention is therefore to address at least one of the problems of the prior art and/or to provide a choice that is useful in the art.

SUMMARY

According to a $1^{st}$ aspect of the invention, there is provided a method for deriving a mental state of a subject, the method comprising: (i) receiving a bio-signal from the subject; (ii) calculating respective statistical variations of at least two physiological parameters derived from the bio-signal; (iii) determining an arousal level of the subject based on the calculated statistical variations of the at least two physiological parameters; (iv) deriving a time-domain heart rate variability signal from the bio-signal for calculating at least two heart rate variability parameters; (v) determining a valence level of the subject based on the at least two heart rate variability parameters; and (vi) deriving the mental state from the arousal level and valence level.

An advantage of the proposed method is that using the two heart rate variability parameters, such as a LF/HF ratio and/or a kurtosis value, and/or HRV coherence, enables a mental state of the subject to be derived more accurately, consequently allowing emotional states of the subject to be tracked over a required time period.

Preferably, the at least two physiological parameters may be selected from the group consisting of respiration rate, heart rate and pulse pressure.

Preferably, receiving the bio-signal may include receiving data related to at least five cardiac cycles of the bio-signal.

Preferably, the method may further comprise using a first of the at least two heart rate variability parameters for determining an initial valence level of the subject, and using a second of the at least two heart rate variability parameters as a conditional threshold parameter for verifying the initial valence level to obtain the valence level in step (v).

Preferably, the at least two heart rate variability parameters may be selected from the group consisting of a heart rate variability coherence of the subject, a LF/HF ratio and a kurtosis value.

Preferably, the heart rate variability coherence may be calculated by correlating the time-domain heart rate variability signal with a reference signal.

Preferably, the LF/HF ratio and kurtosis value may be calculated from a frequency-domain signal obtained from the time-domain heart rate variability signal.

Preferably, the frequency-domain signal may be obtained by converting the time-domain heart rate variability signal into a Power Spectral Density spectrum.

Preferably, the reference signal may include a sine wave representing a time-domain reference signal.

Preferably, the data may include time intervals of the at least five cardiac cycle relating to a systolic peak, start time and end time of each cardiac cycle.

Preferably, the method may further include configuring a machine learning classifier to collectively use the calculated statistical variations for determining the arousal level.

Preferably, the machine learning classifier may include Support Vector Machine, Naïve Bayes or k-Nearest Neighbours.

According to a $2^{nd}$ aspect of the invention, there is provided a computer program for deriving a mental state of a subject, the computer program downloadable to an electronic device and includes a set of instructions, when executed, is arranged to control a processor of the electronic device to: (i) receive a bio-signal from the subject; (ii) calculate respective statistical variations of at least two physiological parameters derived from the bio-signal; (iii) determine an arousal level of the subject based on the calculated statistical variations of the at least two physiological parameters; (iv) derive a time-domain heart rate variability signal from the bio-signal for calculating at least two heart rate variability parameters; (v) determine a valence level of the subject based on the at least two heart rate variability parameters; and (vi) derive the mental state from the arousal level and valence level.

Preferably, the computer program may be downloadable over the internet.

According to a $3^{rd}$ aspect of the invention, there is provided a computer program stored in a memory of an electronic device, the computer program having a set of instructions, when executed, is arranged to control a processor of the electronic device to: (i) receive a bio-signal from a subject; (ii) calculate respective statistical variations of at least two physiological parameters derived from the bio-signal; (iii) determine an arousal level of the subject based on the calculated statistical variations of the at least two physiological parameters; (iv) derive a time-domain heart rate variability signal from the bio-signal for calculating at least two heart rate variability parameters; (v) determine a valence level of the subject based on the at least two heart rate variability parameters; and (vi) derive a mental state of the subject from the arousal level and valence level.

According to a $4^{th}$ aspect of the invention, there is provided an apparatus for deriving a mental state of a subject, the apparatus comprising: (i) a receiver for receiving a bio-signal from the subject; and (ii) a processor for: (a) calculating respective statistical variations of at least two physiological parameters derived from the bio-signal; (b) determining an arousal level of the subject based on the calculated statistical variations of the at least two physiological parameters; (c) deriving a time-domain heart rate variability signal from the bio-signal for calculating at least two heart rate variability parameters; (d) determining a valence level of the subject based on the at least two heart rate variability parameters; and (e) deriving the mental state from the arousal level and valence level.

Preferably, the apparatus may be in the form of an electronic device.

Preferably, the electronic device may be a telecommunications device or a wearable device.

Preferably, the apparatus may include a wearable device and a telecommunications device having a receiver; and wherein the wearable device includes a signal sensing device for obtaining the bio-signal from the subject, and a data processing module for determining data relating to the bio-signal, wherein the receiver of the telecommunications device is arranged to receive the determined data of the bio-signal.

Preferably, the electronic device may include at least one LED and one Photodiode, the LED arranged to emit light onto a surface of the subject and the Photodiode arranged to receive light reflected by the surface of the subject from the emitted light, the reflected light corresponding to the data relating to the at least five cardiac cycles of the bio-signal.

According to a $5^{th}$ aspect of the invention, there is provided a method for determining a valence level of a subject, the method comprising: (i) receiving a bio-signal from the subject; (ii) deriving a time-domain heart rate variability signal from the bio-signal for calculating at least two heart rate variability parameters; and (iii) determining the valence level from the at least two heart rate variability parameters.

Preferably, the at least two heart rate variability parameters may be selected from the group consisting of a heart rate variability coherence of the subject, a LF/HF ratio and a kurtosis value.

According to a $6^{th}$ aspect of the invention, there is provided a method for determining an arousal level of a subject, the method comprising: (i) receiving a bio-signal from the subject; (ii) calculating statistical variation of at least one physiological parameter derived from the bio-signal; and (iii) determining an arousal level of the subject based on the calculated statistical variation of the at least one physiological parameter, wherein the arousal level is determined to be in a stress level if the calculated statistical variation correspond to more than 40% increase in salivary cortisol of the subject.

Preferably, receiving the bio-signal may include receiving data related to at least five consecutive cardiac cycles of the bio-signal.

Preferably, the data may include time intervals of the at least five cardiac cycle relating to a systolic peak, start time and end time of each cardiac cycle.

Preferably, the at least one physiological parameter may include pulse pressure.

Preferably, calculating the statistical variation of the at least one physiological parameter may include calculating the standard deviation of the pulse pressure.

Preferably, the arousal level may be determined to be in the stress level if the calculated standard deviation of the pulse pressure is greater than a threshold value, in which the threshold value is within a range of about 3.0-12.0 mmHg mercury level.

Preferably, the arousal level may be determined to be in the stress level if the calculated standard deviation of the pulse pressure is greater than the threshold value, in which the threshold value is within a range of about 6.0-10.0 mmHg mercury level.

According to a $7^{th}$ aspect of the invention, there is provided a method for deriving a mental state of a subject, the method comprising: (i) receiving a bio-signal from the subject; (ii) calculating respective statistical variations of at least two physiological parameters derived from the bio-signal; and (iii) determining an arousal level of the subject based on the calculated statistical variations of the at least two physiological parameters.

Preferably, the at least two physiological parameters may be selected from the group consisting of respiration rate, heart rate and pulse pressure.

According to an $8^{th}$ aspect of the invention, there is provided a method for determining an arousal level of a subject, the method comprising: (i) receiving a bio-signal from the subject; (ii) calculating statistical variation of at least one physiological parameter derived from the bio-signal; and (iii) determining an arousal level of the subject based on the calculated statistical variation of the at least one physiological parameter, wherein the arousal level is determined to be in a stress level if the calculated statistical variation is greater than a threshold value, in which the threshold value is within a range of about 3.0-12.0 mmHg mercury level.

It should be apparent that features relating to one aspect of the invention may also be applicable to the other aspects of the invention.

These and other aspects of the invention will be apparent from and elucidated with reference to the embodiments described hereinafter.

BRIEF DESCRIPTION OF THE DRAWINGS

Embodiments of the invention are disclosed hereinafter with reference to the accompanying drawings, in which:

FIG. 8 is a table of various parameters showing associated results related to accurately comparing stressful and non-stressful situations;

FIGS. 9a to 9c, shows an improved result for classifying arousal levels by using SVM;

FIGS. 13a and 13b, shows respective diagrams illustrating differences in the HRV coherence and kurtosis value during normal and calm states;

DETAILED DESCRIPTION OF PREFERRED EMBODIMENTS

Figure 3:
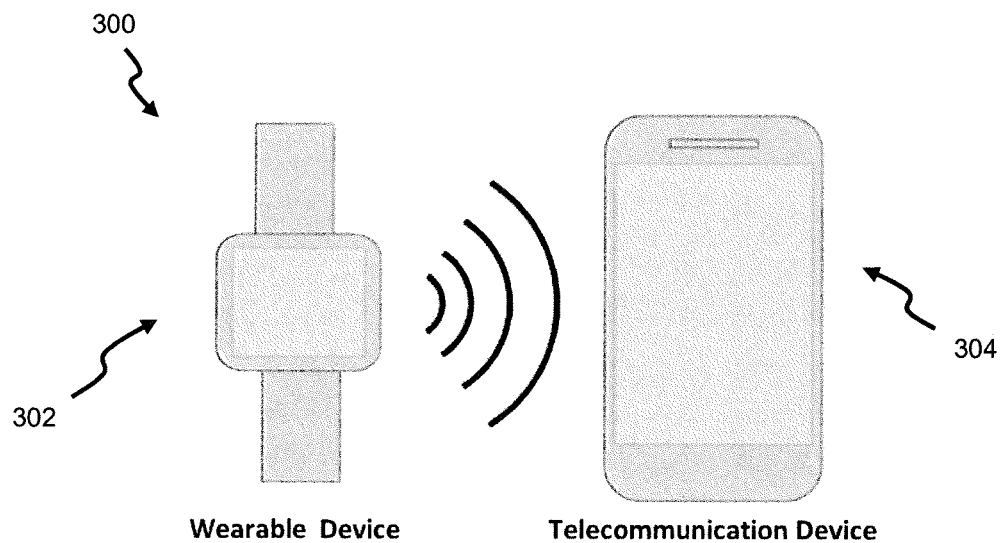
FIG. 3 is a schematic diagram of an apparatus for deriving a mental state of a subject, according to an embodiment of the invention.
Figure 4:
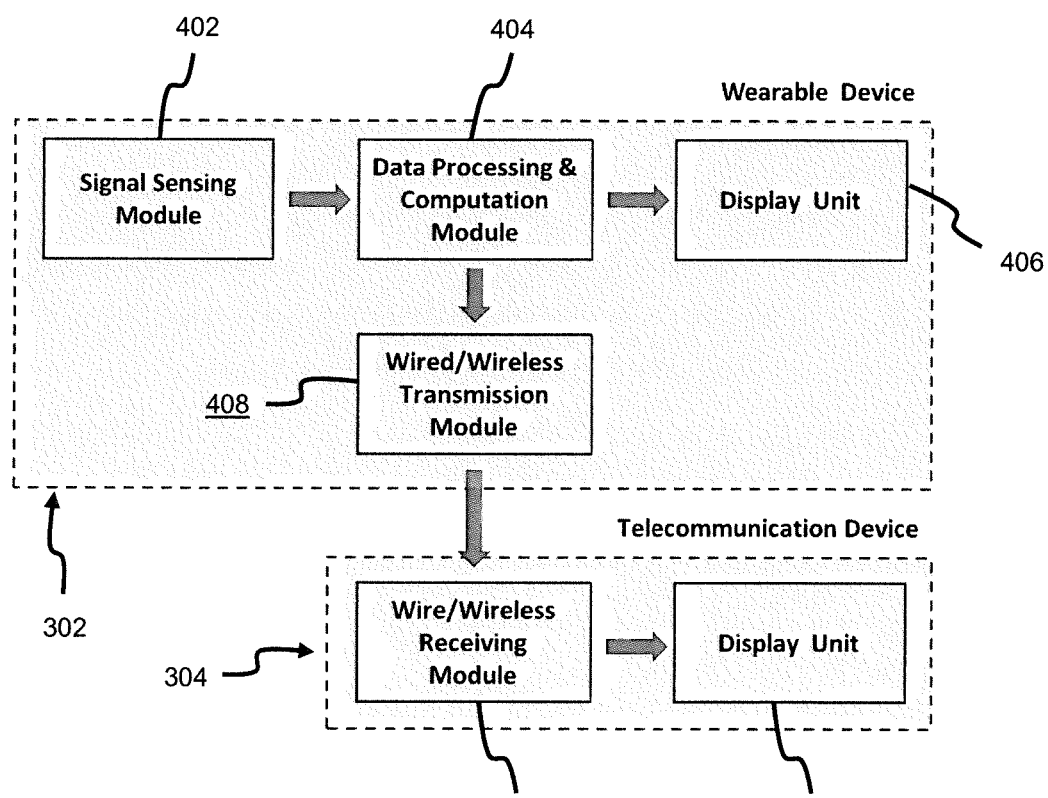
FIG. 4 is a schematic block diagram of the apparatus of FIG. 3.

FIG. 3 is a schematic diagram of an apparatus 300 (comprising a wearable device 302 and a telecommunication device 304) for deriving a mental state of a subject (not shown), according to a first embodiment of the invention. FIG. 4 shows the schematics of the apparatus 300. The subject is a user of the apparatus 300. The wearable device 302 is realisable in different forms, for example as a wrist watch. Of course, it will be appreciated that in other envisaged embodiments, the wearable device 302 may also be in any other form suitable to be worn on any part of a user's body, such as his/her arms, ears, chest, fingers, neck, or foot. In any event, it is to be appreciated that the wearable device 302 is preferably arranged to be conveniently portable, for example in a palm-sized form factor. The wearable device 302 is configured to acquire physiological measurements from a user (wearing the wearable device 302), derive a mental state (which is also known as emotional state) of the said user and then (wired/wirelessly) communicate the derived result(s) to the telecommunication device 304. Examples of the telecommunication device 304 include mobile phones, suitable portable electronic devices, computing devices such as desktop computers, laptop computers, tablets or the like.

Figure 5:
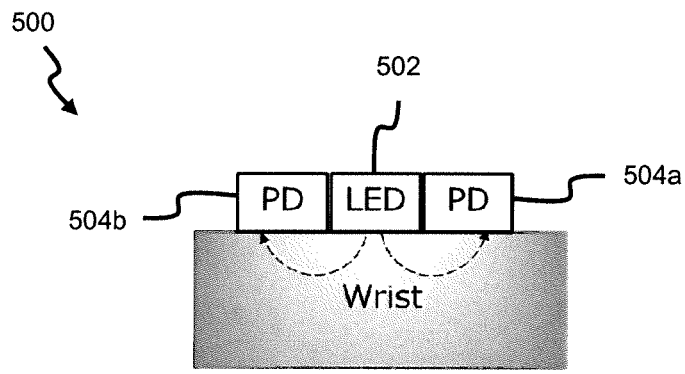
FIG. 5 is a schematic diagram of a LED-PD configuration for a wearable device of the apparatus of FIG. 3.

In respect of FIG. 4, the wearable device 302 includes a signal sensing module 402 for obtaining a bio-signal from the said subject. In this case, the signal sensing module 402 is implemented in the form of an LED-PD module 500 as shown in FIG. 5, but not to be construed as limiting. The LED-PD module 500 includes an LED 502 and two (first and second) PDs 504a, 504b. It is to be appreciated that the term "PD" represents photo diode. Specifically, for the wearable device 302 implemented in the form of a wrist watch, the LED-PD module 500 is configured for taking measurements in reflectance mode. The measurements are based on an amount of light emitted/transmitted by the LED 502 onto a surface (e.g. the wrist, in the case of the wearable device 302 being a wrist watch) of the subject, in which some of the emitted light will subsequently be reflected by the surface as reflected light. This reflected light is then detected by the two PDs 504a, 504b as the bio-signal of the subject. That is, the signal sensing module 402 is thus an optical measurement sensor.

Further, it is to be appreciated that the apparatus 300 also includes other types of physiological parameters sensors (not shown in FIG. 4) such as ECG, EEG, EMG, GSR, temperature sensor and/or pressure sensor that are usable in conjunction with the signal sensing module 402. The different physiological parameters sensors may be arranged separate from the wearable device 302 or integrated therewithin. The different physiological parameters sensors are configured to obtain various physiological parameters (e.g. body temperature and GSR) of the user, and may be positioned on the same or different locations of the user's body (as the wearable device 302) during sensing.

The wearable device 302 further includes a data processing and computational module 404 (hereinafter data processing module for brevity), such as a processor, which is arranged to receive and process the bio-signal acquired by the signal sensing module 402 into an output result. The wearable device 302 also includes a display unit 406 for displaying the output result to the subject. Moreover, the wearable device 302 includes a wired/wireless transmission module 408 arranged to wired/wirelessly communicate the output result to the telecommunications device 304. Needlessly to say, the telecommunication device 304 includes a corresponding wired/wireless receiver module 410 for receiving signals relating to the output results from the wearable device 302 and a display unit 412 for displaying the received results to the subject. For good order, it will be appreciated that a user of the wearable device 302 and telecommunication device 304 may be one same individual or different individuals, but for ease of explanation in this embodiment, it is assumed that the user operating the wearable device 302 and telecommunication device 304 is the same individual.

Figure 15:
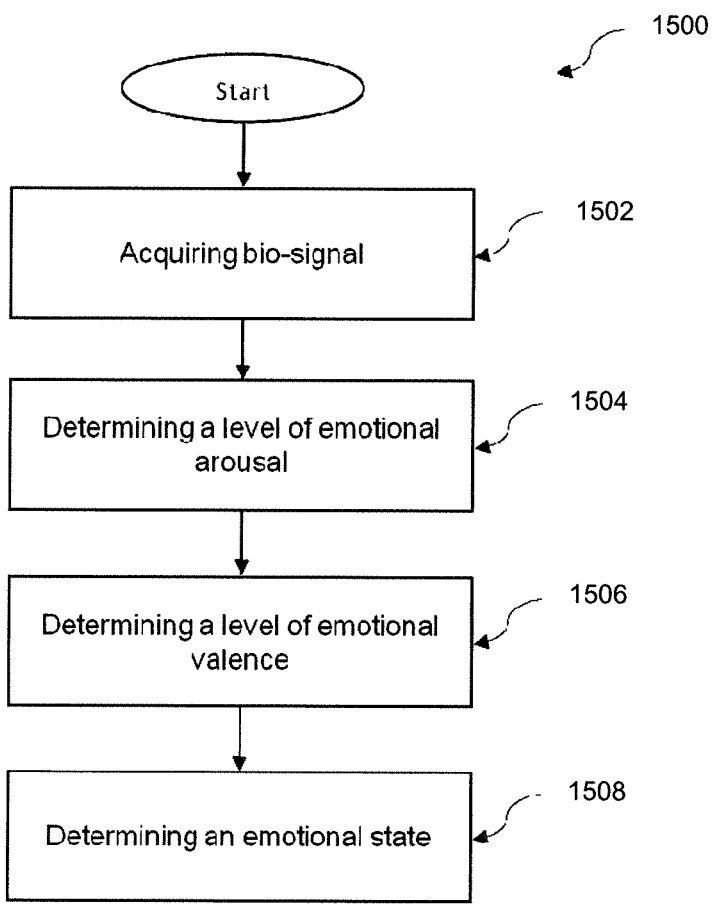
FIG. 15 is a flow diagram of a method, performed by the apparatus of FIG. 1, for deriving a mental state of a subject.

Referring first to FIG. 15, which is a flow diagram 1500 of a method, performed by the apparatus 300 of FIG. 1, for deriving a mental state of a subject, an overview of steps of the said method is briefly outlined with detailed description of each step to follow further below. At step 1502, the subject operates the wearable device 302 to acquire a bio-signal signal of himself, while at next step 1504, an emotional arousal level of the subject is calculated by the wearable device 302, based on the acquired bio-signal. Then at step 1506, an emotional valence level of the subject is calculated by the wearable device 302, also based on the acquired bio-signal. It is to be appreciated that sequence of steps 1504 and 1506 is interchangeable, with no impact on the final results obtained at step 1508. Lastly, at step 1508, the wearable device 302 determines and derives a mental state of the subject based on the calculated arousal level and valence level. The derived mental state is then transmitted in the form of a suitable signal by the wearable device 302 to the telecommunication device 304 to be displayed to the subject himself.

Figure 16:
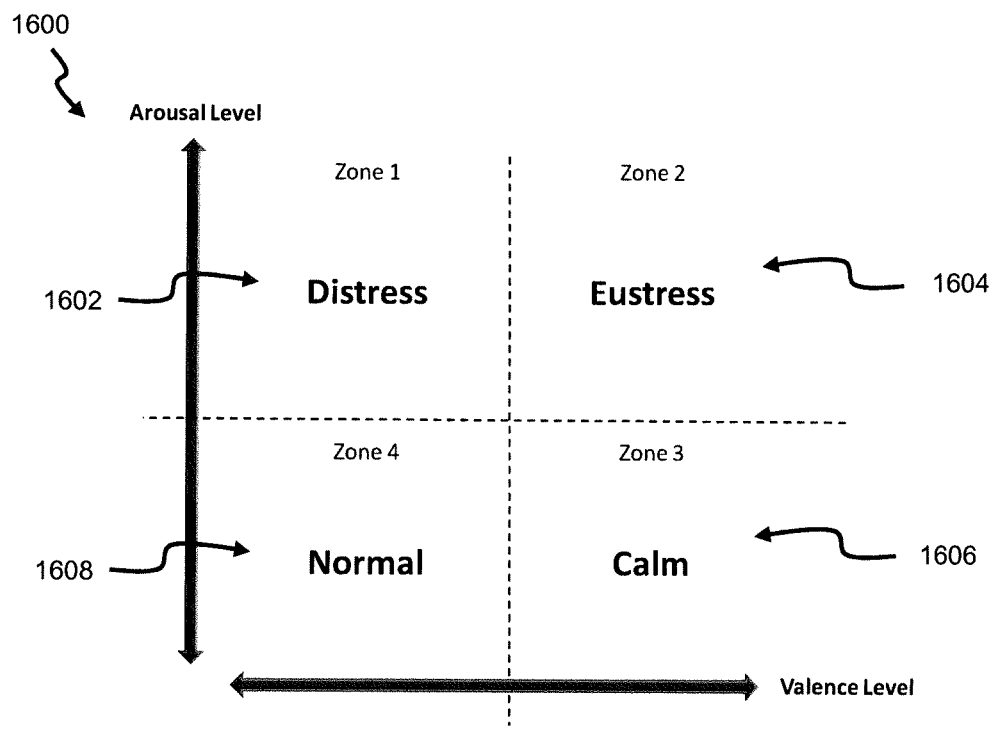
FIG. 16 is a chart diagram used for classifying different levels of arousal and valence into different emotional states.
Figure 17:
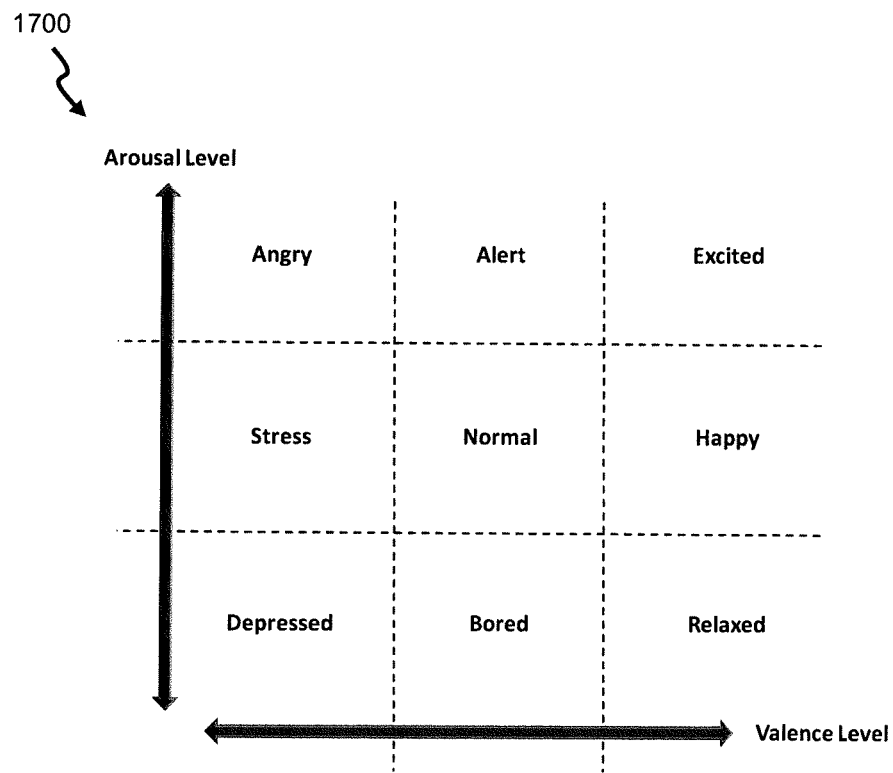
FIG. 17 is a chart diagram used for more detailed classifying different levels of stress and valence into different emotional states.

With reference to step 1508, it is to be appreciated that mental states (i.e. emotions) are classifiable into a multidimensional space by combining obtained results of different levels of arousal and valence, and this multi-dimensional space is depicted in a chart diagram 1600 shown in FIG. 16. Particularly, "Zone 1" 1602 and "Zone 2" 1604 of the multi-dimensional space in FIG. 16 show that if a subject is classified under either zone, then the subject is considered to be in a stressed state. Specifically, "Zone 1" 1602 represents a "Distress" state classification while "Zone 2" 1604 represents a "Eustress" state classification. On the other hand, if the subject is classified under "Zone 3" 1606 or "Zone 4" 1608, then he is considered to be in a non-stressed state. "Zone 3" 1606 represents a "Calm" state classification while "Zone 4" 1608 represents a "Normal" state classification. It is to be appreciated that classification between "Zone 1" 1602 and "Zone 2" 1604 or between "Zone 3" 1606 and "Zone 4" 1608 is determined by a LF/HF (Low Frequency/ High Frequency) ratio, to be further elaborated below. Moreover, to more accurately define overlapping emotions, HRV coherence and kurtosis values are also utilized to further assist with the classification. FIG. 17 shows another chart diagram 1700, in which afore described methods are used to enable a more detailed classification of different levels of arousal and valence into even more levels of emotional states, such as "Angry", "Alert", "Excited", "Stress", "Normal", "Happy", "Depressed", "Bored" or "Relaxed".

The above mentioned steps 1502-1506 of the method in FIG. 15 are now respectively described in greater detail set out below.

Determining a Level of Emotional Arousal

Figure 1:
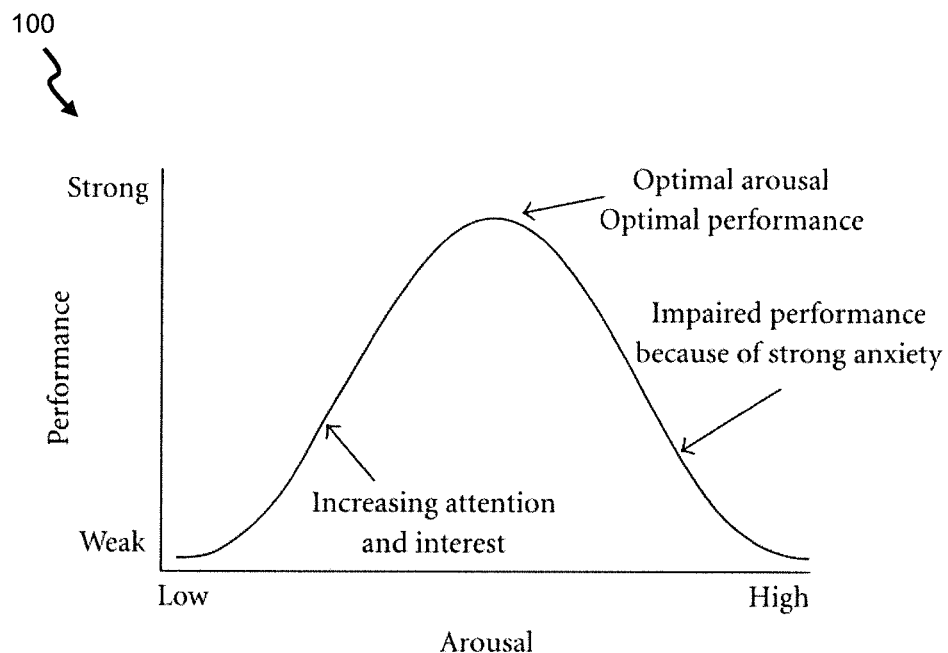
FIG. 1 is a first graph showing an empirical relationship between arousal level and performance, according to the prior art.
Figure 2:
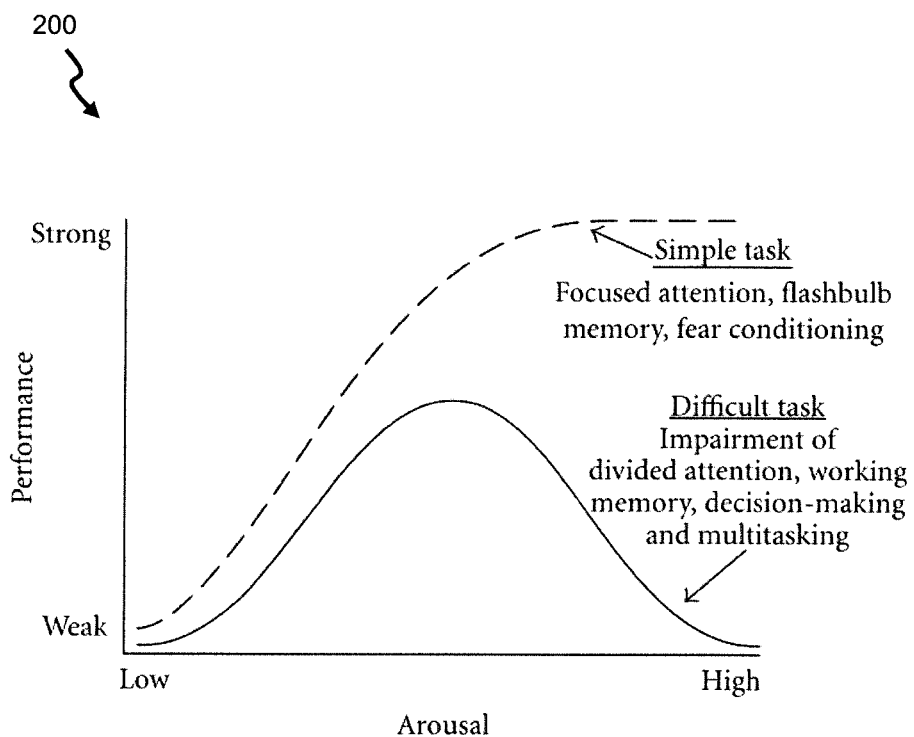
FIG. 2 is a second graph showing an empirical relationship between arousal level and performance of easy and difficult tasks, according to the prior art.
Figure 6:
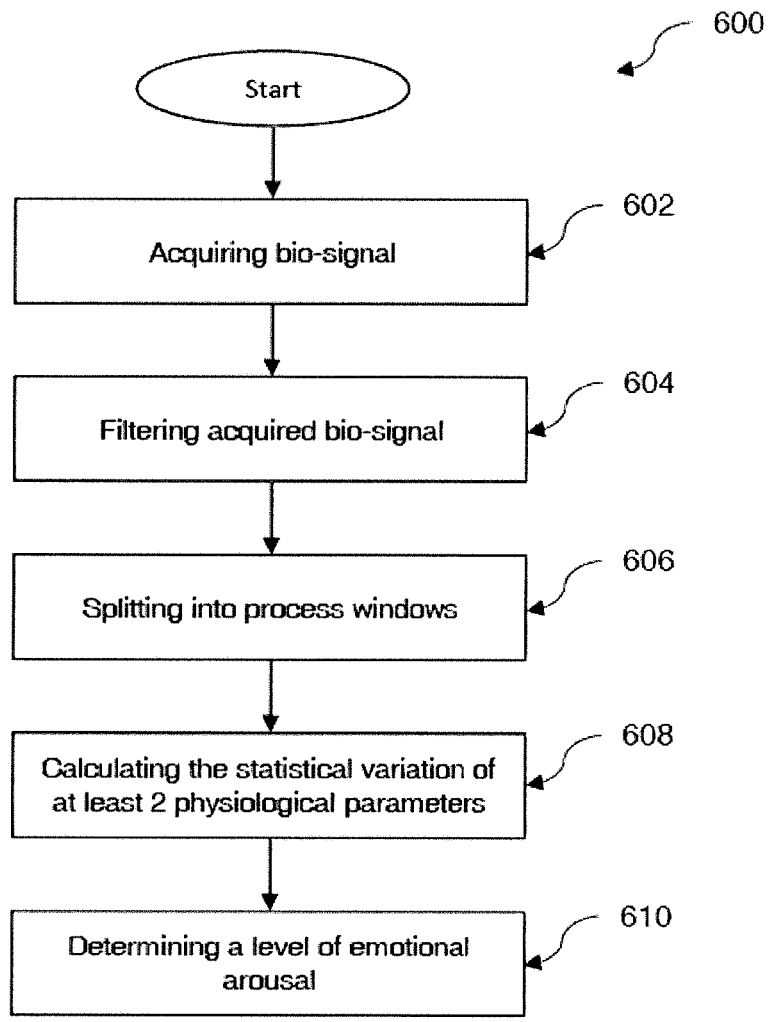
FIG. 6 is a flow diagram of a method, performed by the apparatus of FIG. 1, for determining an arousal level of a subject.

Referring now to FIG. 6, there is shown a flow diagram 600 of a method, performed by the apparatus 300 of FIG. 1, for determining an emotional arousal level of a subject. So it will be appreciated that the method of FIG. 6 in its entirety corresponds to step 1504 of the method in FIG. 15. The method of FIG. 6 is performed according to the following steps. At step 602, a bio-signal is acquired from the subject, which is essentially step 1502 of the method in FIG. 15. Then at step 604, the acquired bio-signal is filtered, and followed by dividing the acquired bio-signal into a plurality of processing windows at step 606. Further, at a next step 608, respective statistical variations (e.g. standard deviation, mean shift, root-mean-square of successive differences (RMSSD) or the like) of the plurality of processing windows (obtained at step 606) relating to at least any two of the following physiological parameters of the subject are calculated: body temperature, skin temperature, galvanic skin response (GSR), respiration rate, heart rate (HR) and pulse pressure (PP). For example, the HR and PP may be selected, and respective standard deviations of the HR and PP (i.e. SDHR and SDPP) are calculated. Of course, if desired, more than two physiological parameters may also be used to enhance the accuracy of the final results obtained at step 610. It is also to be appreciated that some of the physiological parameters are determined from the acquired bio-signal, while certain other physiological parameters are however obtained from the physiological parameters sensors as afore described. Lastly, at step 610, an emotional arousal level of the subject is computed and determined based on the calculated statistical variations of the selected at least two physiological parameters.

Detailed description of each step 602-610 of the method of FIG. 6 is now set out below.

1. Step 602 of the Method

Figure 7:
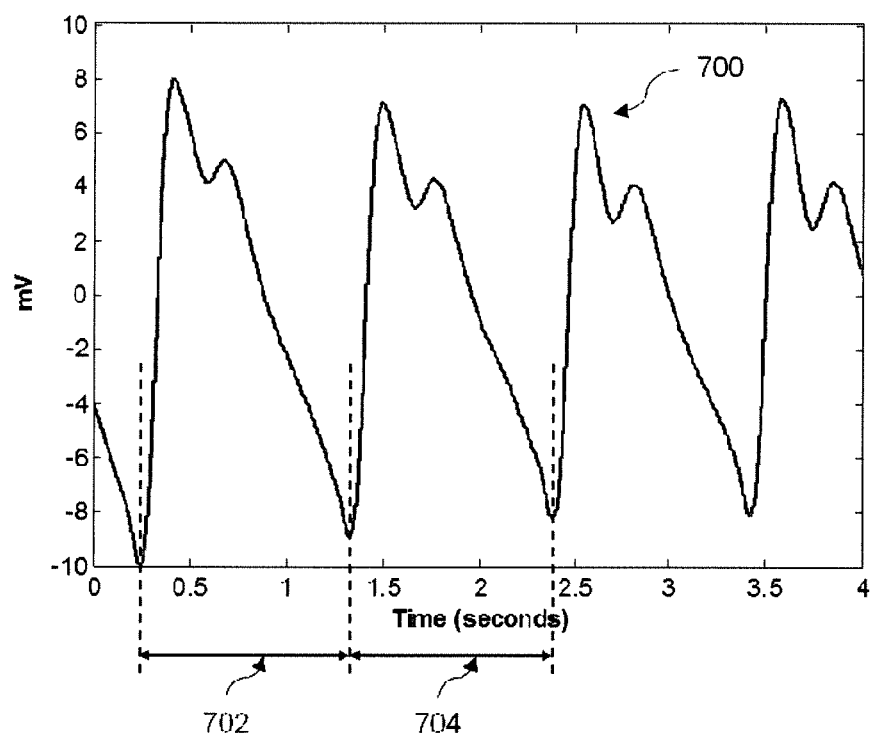
FIG. 7 is a diagram of a PPG signal.

At step 602, signal acquisition is performed by the wearable device 302 using the signal sensing module 402 to obtain the bio-signal and in this embodiment, the bio-signal is an arterial PPG waveform signal 700 (as depicted in an example in FIG. 7) comprising at least five cardiac cycles. That is, the PPG signal 700 is to include at least five cardiac cycles. The at least five cardiac cycles are also arranged consecutively. The PPG signal 700 includes time intervals of the at least five cardiac cycle relating to a systolic peak, start time and end time of each cardiac cycle. The PPG signal 700 may be acquired from any peripheral sites of a subject's body such as the wrist and/or finger. It has been empirically determined that an accuracy suitable for acquiring the subject's bio-signal may for example, but without being limiting, be achieved by configuring the signal sensing module 402 to employ a 180 seconds measurement window to obtain the subject's bio-signal.

2. Step 604 of the Method

The acquired PPG signal 700 is next passed to the data processing module 404 for processing and calculation. The data processing module 404 may include a predefined digital band pass filter (not shown) for filtering noise and artifacts from the acquired PPG signal 700 to produce a filtered PPG signal (not shown).

3. Step 606 of the Method

At step 606, the filtered PPG signal is then segmented into a plurality of processing windows to facilitate subsequent processing. But of course, segmenting the filtered PPG signal into the plurality of processing windows may not be necessary in other embodiments, if not desired. In such instances, a statistical variation of the whole measurement window (used in step 602 to acquire the subject's bio-signal) is then computed instead. Going back to this embodiment, each processing window is arranged to include at least five (consecutive) cardiac cycles, and since it is described in step 602 that the PPG signal 700 is to include at least five cardiac cycles arranged consecutively, this thus means that there is a minimum of one processing window to result from step 606. The size of a processing window is defined as a specified time duration of said window, but to be understood is an example and therefore not to be construed as being the only definition possible. For instance, relating to calculating the subject's SDPP and SDHR, it has been determined that an accuracy suitable for calculating the SDPP and SDHR may for example, but without limitation, be achieved by utilizing a predetermined window size of about 30 seconds depending on specific accuracy requirement. The size of each processing window may also be adaptively configured during the segmenting process so that more cardiac cycles (i.e. more than five) are included in each processing window to ensure high accuracy of results.

4. Step 608 of the Method

For step 608, as mentioned, the respective statistical variations (e.g. standard deviation, mean shift, root-mean-square of successive differences (RMSSD) or the like) of the plurality of processing windows (obtained at step 606) relating to at least any two of the following physiological parameters of the subject are calculated: body temperature, skin temperature, galvanic skin response (GSR), respiration rate, heart rate (HR) and pulse pressure (PP). For example, the HR and PP may be selected, and respective standard deviations of the HR and PP (i.e. SDHR and SDPP) are calculated. Conventional methods are used for calculating the statistical variations, and hence will not be elaborated herein for brevity sake.

5. Step 610 of the Method

At step 610, the calculated statistical variations obtained from step 608 (or just a single statistical variation, if the entire measurement window is instead utilized for the calculation) are provided to a machine learning classifier for classification into different arousal levels. Any known machine learning classifier such as Support Vector Machine (SVM), Naive Bayes, k-Nearest Neighbors (KNN) or the like may be used independently/in combination for classification of the arousal levels, provided the classifiers to be adopted are pre-trained using same/similar parameters to be used for the classification using clinical test results. In this embodiment, SVM is selected as the classifier to be used, due to the robustness and high accuracy performance of SVM.

As mentioned, the pulse pressure may be selected as an example of one of the physiological parameters to be used, and SDPP may be used because of the significant difference determined in related measurement values for stressful and non-stressful situations. Hence, a more accurate differentiation between stressful and non-stressful situations is possible using SDPP. FIG. 8 is a table 800 depicting a list of parameters and respective associated classifying performance from a clinical study performed. It will be appreciated from the said table 800 that a low p-value obtained for SDPP clearly shows the most significant differences in value between the stressful and non-stressful situations.

Figure 9:
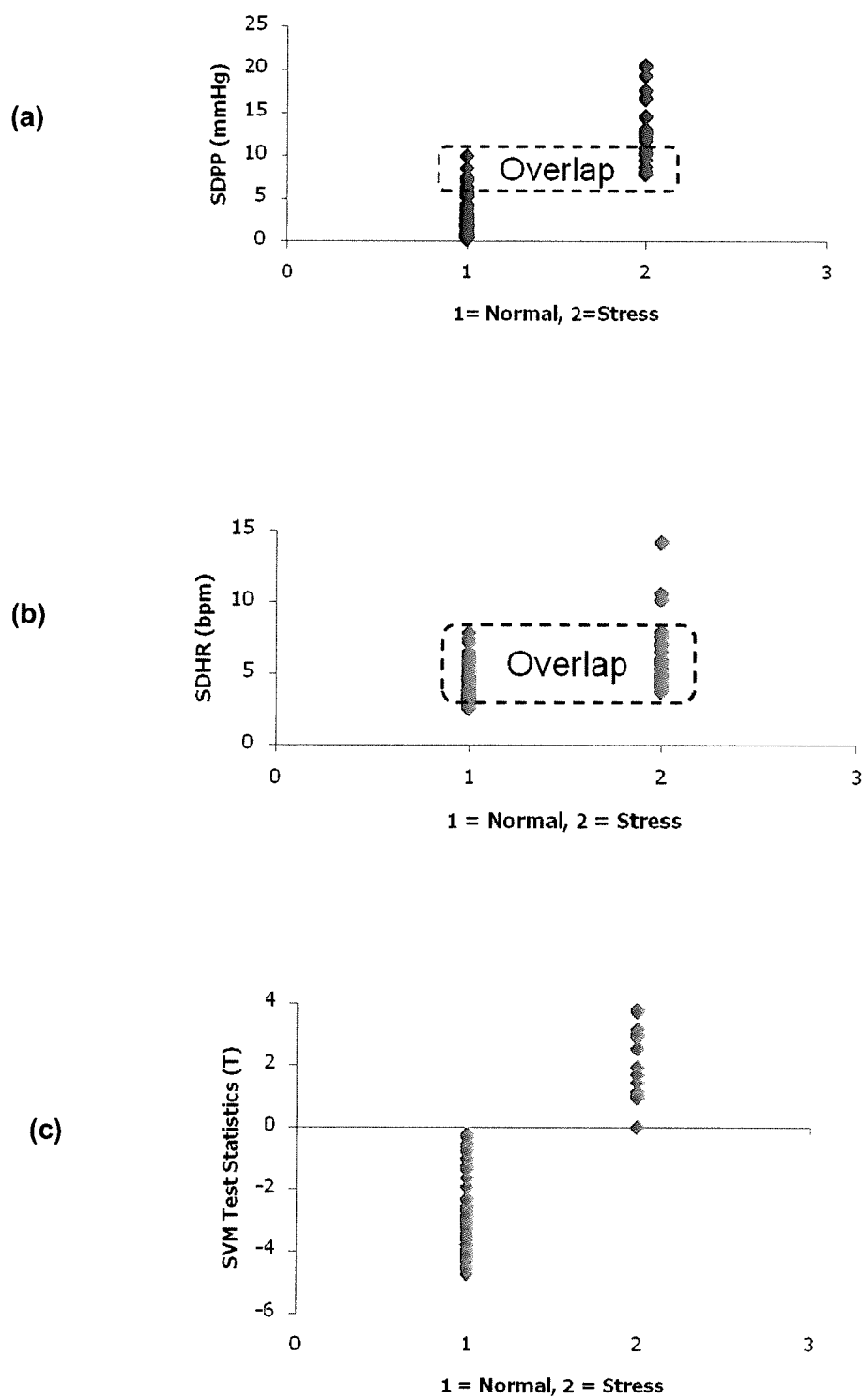
FIG. 9, which includes

While SDHR and SDPP may be selected (as examples) for use in the method of FIG. 6, FIG. 9a and FIG. 9b illustrate that there are still however overlapping data in each parameter that cannot be used to accurately classify between stressful and non-stressful situations. To address this issue, the SVM classifier is utilized to also classify the overlapping classes of data. The improved results are shown in FIG. 9c in which the trained SVM classifier is substantially able to distinguish between stressful and non-stressful situations.

Determining a Level of Emotional Valence

Figure 10:
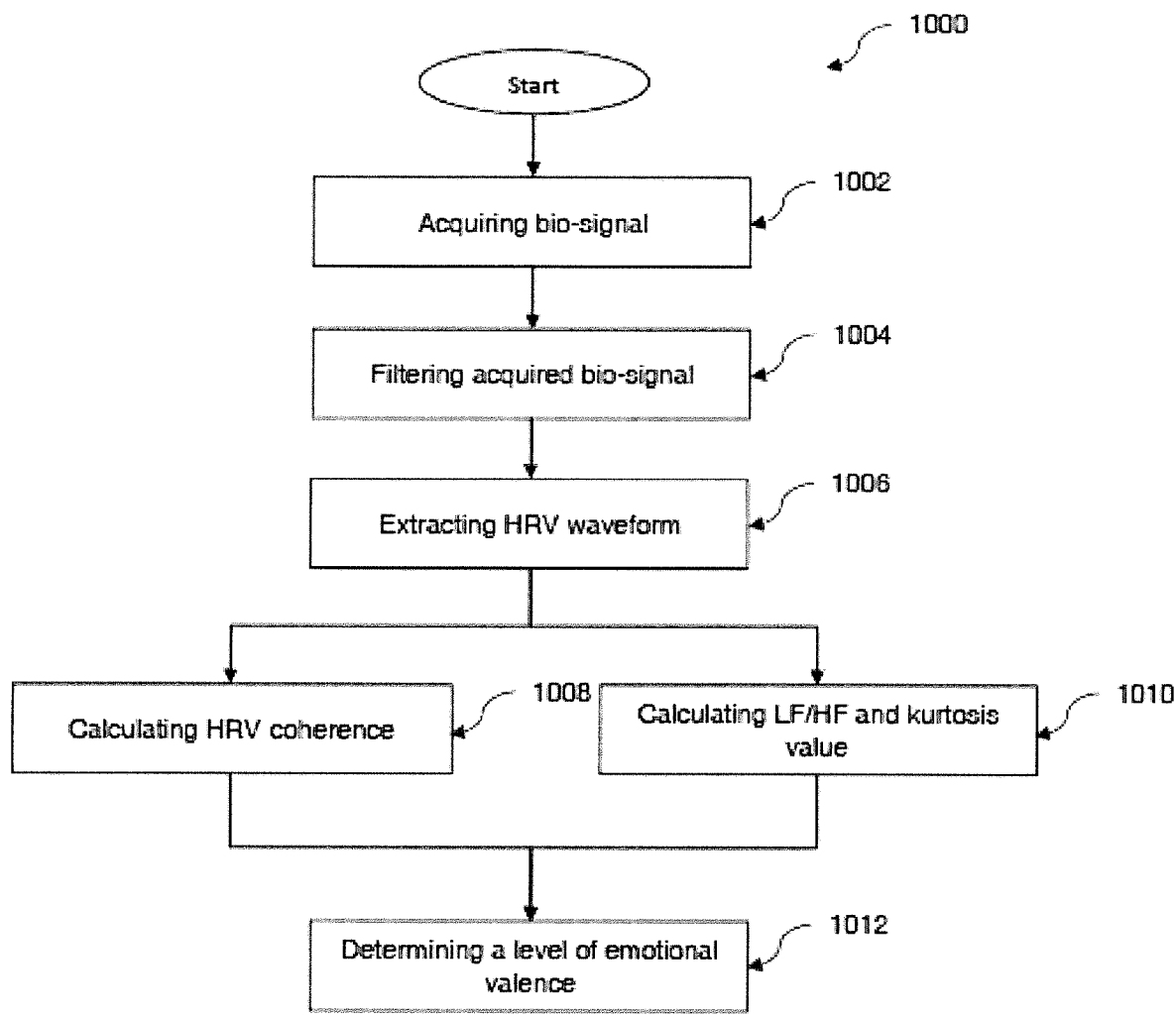
FIG. 10 is a flow diagram of a method, performed by the apparatus of FIG. 1, for determining a valence level of a subject.

Moving to FIG. 10, there is shown a flow diagram 1000 of a method, performed by the apparatus 300 of FIG. 1, for determining a valence level of the subject. It will be appreciated that the method of FIG. 10 in its entirety corresponds to step 1506 of the method in FIG. 15. The method of FIG. 10 is performed according to the following steps. At step 1002, the bio-signal signal is acquired, which is essentially step 1502 of the method in FIG. 15. So, steps 602 and 1002 are in fact just step 1502 of FIG. 15. Then at step 1004, the acquired bio-signal is filtered, and followed by extracting a time-domain heart rate variability (HRV) signal from the acquired bio-signal at step 1006. At step 1008, a HRV coherence of the subject is calculated by correlating the HRV signal with a reference signal. The reference signal is, for example, a sine wave representing a time-domain reference signal. Next, at step 1010, a frequency domain analysis is performed (using Fast Fourier Transform (FFT) algorithm) on the time-domain HRV signal to derive a PSD graph to calculate at least one related frequency-domain parameter. The at least one frequency-domain parameter includes a LF/HF (Low Frequency/High Frequency) ratio and a kurtosis value, but in alternative embodiments, other suitable features may also be included. Lastly, at step 1012, a valence level of the subject is determined (in this instance) based on the calculated HRV coherence, LF/HF ratio, and kurtosis value. It is to be appreciated that the HRV coherence, LF/HF ratio, and kurtosis value may also collectively be termed as HRV parameters/features.

It is to be appreciated that step 1004 is, mutatis mutandis, similar to step 604 of the method of FIG. 6 (as afore described), and hence for sake of brevity, the explanation will not be repeated. Detailed description of the subsequent steps 1006-1012 of the method of FIG. 10 is now set out below.

1. Steps 1006 and 1008 of the Method

For steps 1006 and 1008, the teachings of a PCT application, having publication number WO2014/031082, is incorporated in its entirety herein. Hence, the interested reader is directed to the afore said PCT application WO2014/031082 for full details on how to derive a time-domain HRV signal from the bio-signal for subsequently correlating with a reference signal in order to obtain the HRV coherence of the subject. Of course, it is to be appreciated that any other known methods for calculating the HRV coherence (whether in time or frequency domain) may also be used, and not just limited to only the method described in PCT application WO2014/031082.

2. Step 1010 of the Method

Figure 11:
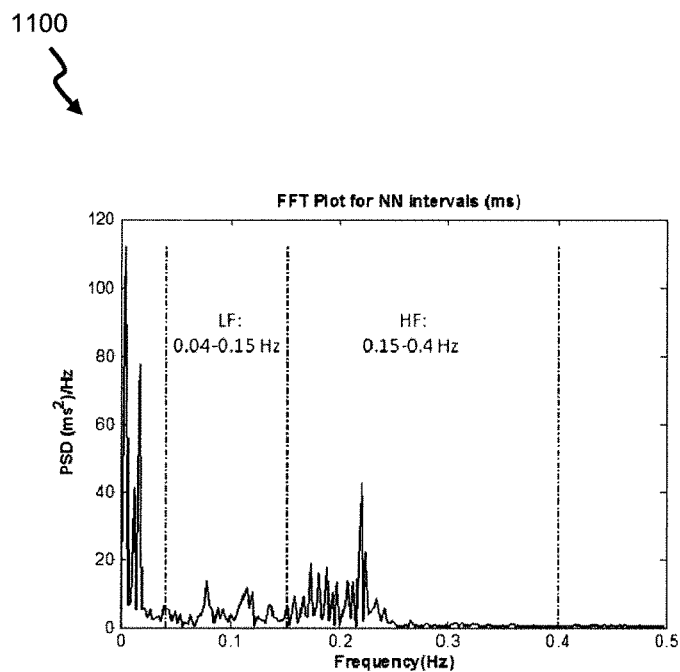
FIG. 11 is a graph showing a PSD spectrum.

At step 1010, by utilizing the Fast Fourier Transform (FFT) algorithm, the time-domain HRV signal is converted into a Power Spectral Density (PSD) graph by the data processing module 404, in which an example graph 1100 of a PSD is shown in FIG. 11. That is, the PSD graph is a frequency-domain spectrum obtained from the time-domain HRV signal. Specifically, the low frequency (LF) power (i.e. 0.04-0.15 Hz) and the high frequency (HF) power (i.e. 0.15-0.4 Hz) bands of the PSD graph are quantified by mathematical integration of the PSD graph, which are then utilized by the data processing module 404 to calculate a ratio of the low frequency power to the high frequency power (LF/HF). Further, a spectral kurtosis analysis is performed by the data processing module 404 on the PSD graph to calculate a kurtosis value.

3. Step 1012 of the Method

Figure 12:
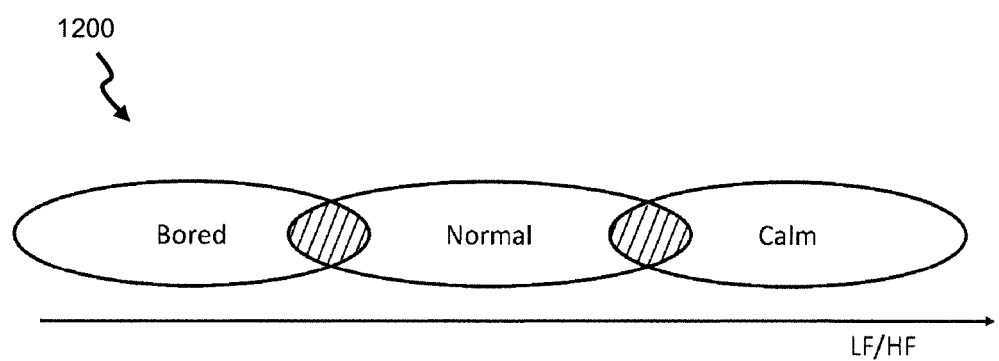
FIG. 12 is a Venn diagram illustrating overlapping relationships between different emotions classification.
Figure 13:
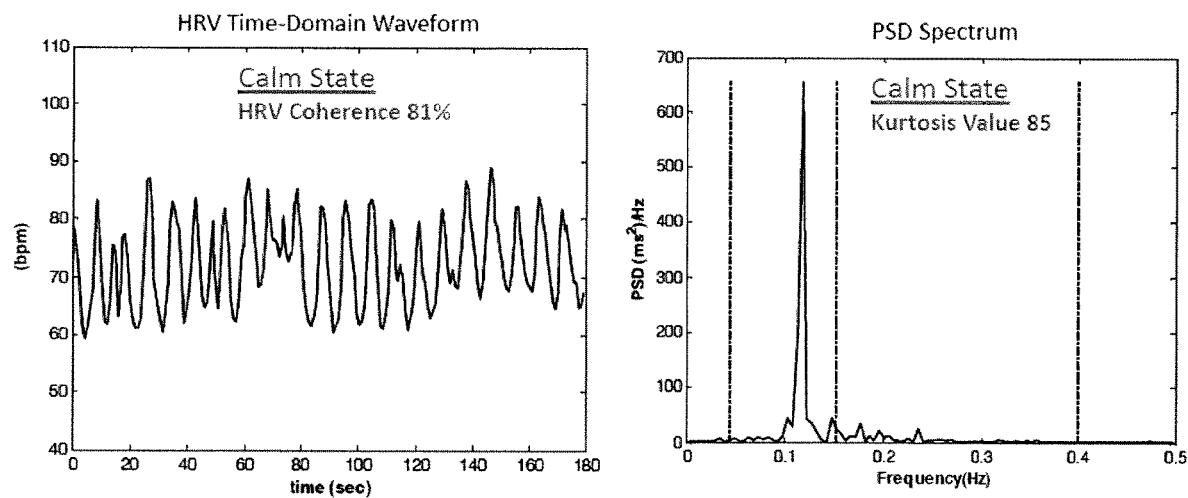
FIG. 13, which includes
Figure 13:
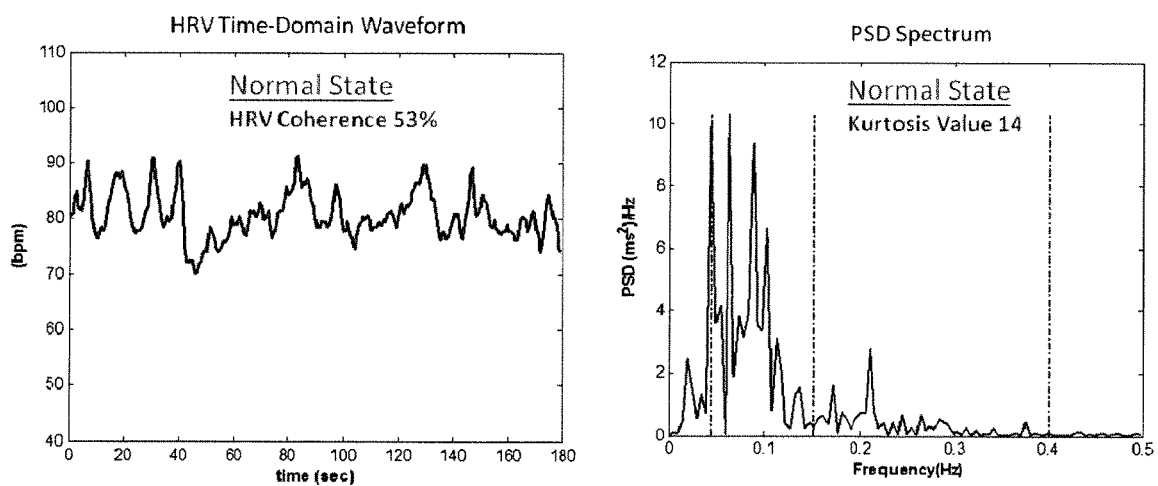

It is to be appreciated that the LF/HF ratio is commonly used to differentiate emotions of different levels of valence. But as depicted in shaded portions of a Venn diagram 1200 in FIG. 12, there is still overlapping of closely related emotions based on a same value of LF/HF ratio. Apart from the LF/HF ratio, the HRV coherence is also determined to be closely related to the (emotional) valence level. For the kurtosis analysis of the PSD, as shown in FIGS. 13a and 13b, the kurtosis value is found to be highly related to the HRV coherence of an individual. For this embodiment, it is thus determined that a combined analysis of the HRV coherence, LF/HF ratio and kurtosis value provides the highest accuracy in determining a valence level of the subject.

Figure 14:
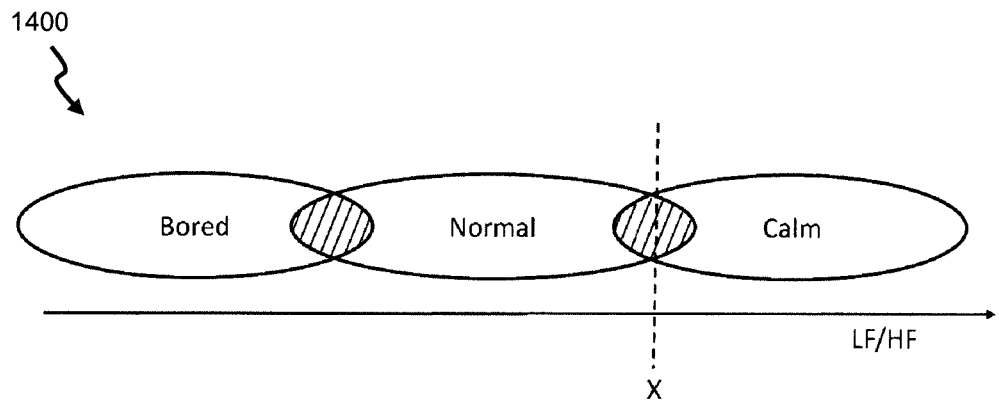
FIG. 14 is a Venn diagram illustrating a method of using different HRV features for determining a valence level.

So, at step 1012, the valence level is derived collectively from the HRV coherence, LF/HF ratio and kurtosis value. As mentioned, a value of the LF/HF ratio typically indicates a corresponding emotional valence of a subject but it is to be appreciated that a boundary that separates closely related emotional states (i.e. see FIG. 16 or FIG. 17) is still vague. Nonetheless, an initial level of the valence is still determinable. Subsequently, the HRV coherence and kurtosis value are used to further assist with verifying that the initially determined valence level is correct. For example, if the subject is in a calm state (i.e. high autonomic balance), the valence level is characterized by a high LF/HF ratio. To illustrate, with reference to a Venn diagram 1400 in FIG. 14, a subject who is in a normal state but is determined to have a higher value of the LF/HF ratio may otherwise be mistaken to be in a calm state. Indeed, by incorporating the HRV coherence and kurtosis values (whether individually or combined) into the analysis as threshold parameters (which are compared against threshold values), it may then be further verified whether the subject is truly in a calm state. For good order, it is to be appreciated that the threshold values are predetermined empirically from clinical tests. For example, the following set of inequality equations may be used to determine whether a calculated valence level falls in the normal region: IF "calculated LF/HF>X", "calculated Kurtosis<A" and "calculated HRV Coherence<B", THEN "Valence Level=Normal", in which variables "A" and "B" represent the predetermined threshold values, while "X" represents just a predetermined value.

The remaining configurations will be described hereinafter. For the sake of brevity, description of like elements, functionalities and operations that are common between the different configurations are not repeated; reference will instead be made to similar parts of the relevant configuration(s).

In a second embodiment, instead of being two separate devices (i.e. the wearable device 302 and telecommunication device 304), the apparatus 300 itself may be implemented as a single equivalent electronic device, in which the wearable device 302 and telecommunication device 304 are (hardware) integrated and configured to perform all the same functions described in the first embodiment. Further, all the steps 1502-1508 in the flow diagram 1500 of FIG. 15 (which thus also include steps 602-612 in the flow diagram 600 of FIG. 6, and steps 1002-1012 in the flow diagram 1000 of FIG. 10) may be implemented as a computer program product downloadable over the internet for storing on a memory of the said electronic device. In other words, if there are improvements to the method of FIG. 15, the electronic device may also be updated (as and when required) with those improvements by way of the downloaded computer program product.

In a third embodiment, all the steps 1502-1508 in the flow diagram 150 of FIG. 15 may be performed by one electronic device which may be the telecommunications device 304 (instead of the wearable device 302), or other envisaged suitable electronic devices. In other words, it is envisaged that the various modules—signal sensing, data processing module 402, 404 may form parts of the same electronic device, possibly as part of the telecommunications device 304. As a result, there is no longer any necessity for the wired/wireless transmission module 408 or wired/wireless receiver module 410 in such a configuration. Needless to say, the single electronic device may also be realised as a wearable sensing device to be worn on the subject's body.

In a fourth embodiment, steps 1504-1508 of the method in FIG. 15 may alternatively be performed by a data processing module (not shown) of the telecommunications device 304, instead of the wearable device 302, if it is determined (for example) that the data processing module of the telecommunications device 304 possesses a higher processing power than that of the wearable device 302, but however not to be construed as a limiting. Furthermore, performance of steps 1504-1508 of FIG. 15 may also dynamically be allocated between the data processing module of the telecommunications device 304, and the data processing module 404 of the wearable device 302, depending on a desired configuration effected by a user of the apparatus 300. In summary, via the method of FIG. 15 (which is performed by the proposed apparatus 300 of FIG. 3), a valence level of a subject is obtained from a HRV signal thereof. Both the time and frequency domains of the HRV signal are utilized during the process. Specifically, from the time-domain, a HRV coherence of the subject is determined. Also, a PSD graph is obtained by converting the HRV signal from the time-domain to the frequency-domain. Therefrom, a LF/HF ratio and a kurtosis value are derived from the PSD graph. Subsequently, by analysing the HRV coherence, LF/HF ratio and kurtosis value in combination, a valence level of the subject is determined. In addition, an emotional arousal level of the same subject is also determined from the statistical variations of the heart rate and pulse pressure of the subject. But as afore discussed, any other two physiological parameters from the group: body temperature, skin temperature, galvanic skin response (GSR), respiration rate are selectable as well. A machine learning classifier (e.g. SVM) that has been trained to classify different arousal levels using the same afore parameters is used to determine an arousal level of the subject based on (for example) the measured statistical variations of heart rate and pulse pressure. Based on the determined valence and arousal levels of the subject, a mental state of the user is consequently derived.

Figure 18:
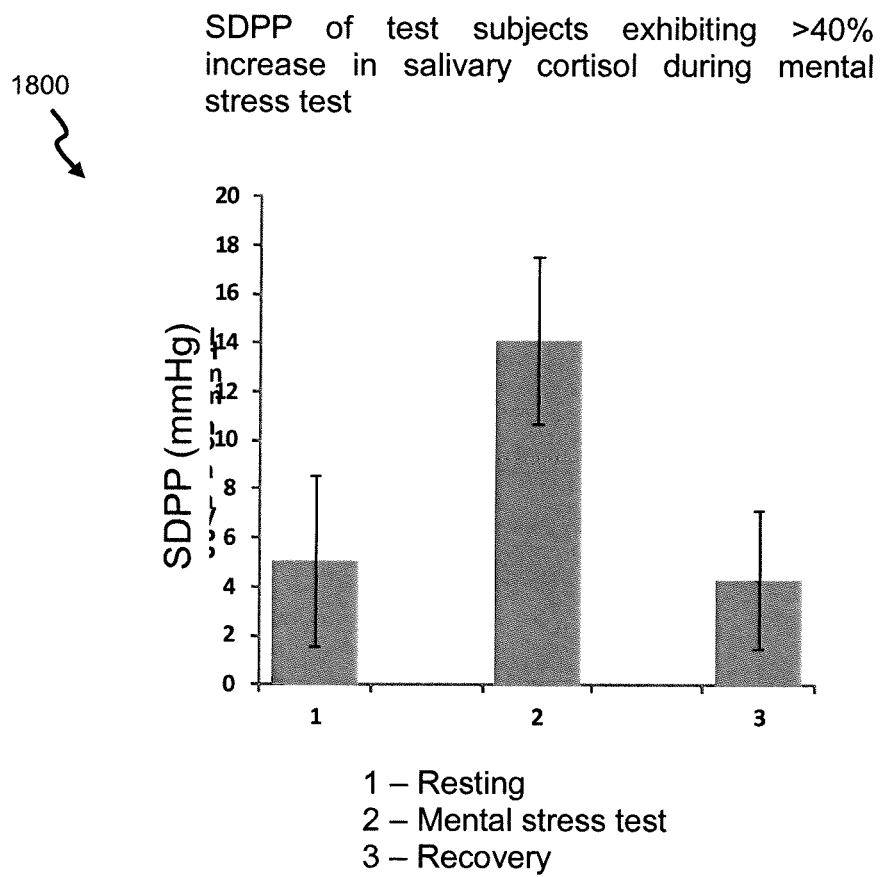
FIG. 18 is a table of measured mercury levels associated with the SDPP parameter as empirically obtained under stressful and non-stressful situations.

In a fifth embodiment, at step 610 of the method of FIG. 6, an alternative to providing the calculated statistical variations (obtained from step 608) to the machine learning classifier for classifying into different arousal levels, is instead utilised. Specifically, FIG. 18 is a table 1800 of measured mercury level associated with the SDPP parameter as empirically obtained under stressful and non-stressful situations, in relation to classifying performance based on a clinical study using salivary cortisol as an indicator for stress conditions. According to the study result, the standard deviation for pulse pressure (PP) of test subjects is observed to be higher during stressful conditions (i.e. see legend label: "2—Mental stress test" in FIG. 18) corresponding to more than 40% increase (i.e. >40%) in salivary cortisol, as compared to non-stressful conditions (i.e. see legend labels: "1—Resting", and "3—Recovery" in FIG. 18). Particularly, it is to be appreciated that for SDPP, the more than 40% increase (i.e. >40%) in salivary cortisol empirically corresponds to a cut-off threshold range of about 3.0-12.0 mmHg mercury level measured, and more specifically, that range may further be within a range of about 6.0-10.0 mmHg mercury level. Preferably, a cut-off threshold value of about 8.0 mmHg mercury level may beneficially be used as an accurate indicator, if necessary. So, using the said cut-off threshold value, the machine learning classifier is thus not required in this embodiment.

Then drawing reference to FIG. 16, it consequently means that the determined arousal level of a subject moves from "Zone 4" 1608 to "Zone 1" 1602, if there is a measured >40% increase in salivary cortisol of the subject. Accordingly, the good correlation results show that PP may serve as a good substitute parameter for salivary cortisol testing for stress. Hence, in this embodiment, (occurrence of) stress is defined as corresponding to detection of >40% increase in salivary cortisol. Following from the preceding statement, it may broadly be generalised that the arousal level of a subject is determined to be in a stress level, if the calculated statistical variation of at least one physiological parameter (e.g. PP) corresponds to more than 40% increase in salivary cortisol of the subject. Also, it may be said to the same effect that the arousal level is determined to be in a stress level if the calculated statistical variation is greater than a threshold value, in which the threshold value is within a range of about 3.0-12.0 mm Hg mercury level. The threshold value may be about 8.0 mmHg mercury level, for example. Specifically, the calculated standard deviation of the pulse pressure is determined to correspond to a range of about 3.0-12.0 mmHg mercury level in order to determine that the arousal level is in the stress level (i.e. >40% increase in salivary cortisol). More preferably, the calculated standard deviation of the pulse pressure is determined to correspond to a threshold value of about 8.0 mmHg mercury level, under such an instance. Also, to reiterate, the method 600 of FIG. 6 may be carried out independent of the method 1500 of FIG. 15. Further, the apparatus 300 of FIG. 1 may also be configured to provide an independent readout of the determined arousal level (i.e. via the display unit 406 of the wearable device 302), if necessary.

Applications

The proposed apparatus 300 beneficially provides a tracking solution for individuals to track their emotional states over a desired time period (in which the apparatus 300 may be programmed to enable automatic tracking for that time period). This enables the individuals to recognize situations which can cause emotional changes to them so that the individuals are able to learn to cope with those situations better in the future. The time period is configurable to be any duration, such as the past hour or last 24 hours, last 7 days or last 1 month, as intended by the individuals. Data generated by the apparatus 300 from the tracking, during the required time period, may be presented to the individuals in textual or graphical format such as trends displayed as bar or pie charts.

Also, the proposed apparatus 300 may provide individuals with bio-feedback, trainings or interventions to assist with managing stress or improving into one of the healthy mental states. One example is using breathing training to improve the HRV coherence as taught in the PCT application, having publication number WO2014/031082. Briefly, the wearable device 302 may also include an audio output module (e.g. in the form of a speaker), in which instructions for the breathing training are given to users via the display unit 406 and the audio output module. Of course, the instructions for the breathing training may also be administered through the telecommunication device 304 or any other suitable external devices. Other examples include configuring audio/visual stimulations (effected via the apparatus 300) to assist an individual to relax, and/or using interventions (similarly effected via the apparatus 300) such as generating vibrations, alerts and/or emails to alert the individual of prolonged stress exposures.

Further, the apparatus 300 is able to help with monitoring and altering emotions, and, as will be appreciated, is thus especially useful in situations where emotions plays an important part to the outcome of a situation in concern. As different tasks require varying levels of emotional arousal and valence, using the apparatus 300 therefore allows individuals to more easily and knowingly alter their emotions so that their performance of the related tasks may greatly be enhanced. As an example, by using the apparatus 300, it may help working adults/students detect and decrease their arousal level at any time they think is hampering their related performance, such as attention level or creative thinking. Similarly, companies may use the proposed apparatus 300 to help monitor the emotional states of their staffs, such as whether a particular staff is facing problem(s) like a burnout or is lacking motivation (i.e. low arousal) to perform his/her job well, and accordingly determine whether remedy measures are required to help that staff.

As another example, say in a physician-patient relationship setting, the patient may also use the apparatus 300 to monitor and manage his/her emotions, while the physician may beneficially track the patient's emotion states over a period of time and/or correlate with other behavioural data, such as activity and sleep tracking data, for making better diagnosis for effective treatment.

The proposed apparatus 300 is also beneficially applicable to the sports sector. While it is important for athletes to be psyched up (i.e. positively aroused) to achieve optimum performance during competitions, it is entirely a different matter if the athletes are attempting to learn/master a new skill/technique, where a calm mind (i.e. low arousal, and positive valence) is more beneficial. For coaches, on the other hand, being able to analyse the emotional states and trends of their athletes may be useful for understanding the effectiveness of trainings conducted, as well as aiding the coaches with selecting suitable athletes for participating in competitions.

As a comparison, while there are many conventional devices that enable users to measure their own emotional levels, most of these devices however based measurements only via a single common parameter such as the HRV, unlike the proposed apparatus 300 of FIG. 3. Hence, the knowledge gap that exists in conventional solutions is advantageously addressed by the apparatus 300 of FIG. 3, which purposively utilises the complex relationship between physiological parameters and emotional states for accurate determination of the emotional well-being of an individual.

While the invention has been illustrated and described in detail in the drawings and foregoing description, such illustration and description are to be considered illustrative or exemplary, and not restrictive; the invention is not limited to the disclosed embodiments. Other variations to the disclosed embodiments can be understood and effected by those skilled in the art in practising the claimed invention. For example, the LED-PD module 500 of FIG. 5 may alternatively also include a plurality of similar LEDs 502 paired with one or multiple PDs. That is, the basic configuration of the LED-PD module 500 includes at least one LED and one PD. In addition, for the method in FIG. 10, the least one threshold value may also include a combination of other suitable parameters, other than the LF/HF ratio and kurtosis value. Yet moreover, in certain embodiments, either only the LF/HF ratio or kurtosis value may be used together with the HRV coherence to derive the valence level, even though the results obtained may be less accurate. Furthermore, only one of the LF/HF ratio or kurtosis value or HRV coherence may be used to derive the valence level, if desired. Also, at step 608 of FIG. 6, an average statistical variation may alternatively be obtained by averaging all computed statistical variations of the plurality of processing windows. Then, this average statistical variation is provided (at step 610) to the machine learning classifier for classification into different arousal levels.

Moreover, to derive the valence level, at least any two HRV parameters may be selected from the group comprising of the HRV coherence, LF/HF ratio, kurtosis value and other suitable parameters may be used in certain embodiments. In such cases, a first of the selected two HRV parameters may be used for determining an initial valence level of the subject, and a second of the selected two HRV parameters may then be used as a conditional threshold parameter for verifying the initial valence level to obtain the final valence level (at step 1012 of FIG. 10). For example, the HRV coherence is used (e.g. instead of LF/HF) to define an initial valence, while the kurtosis value and/or the LF/HF ratio are/is used as conditional thresholds to further assist with the verification. In another example, the LF/HF ratio is used to define an initial valence, while only the kurtosis value is used as a conditional threshold for the verification.

The invention claimed is:

1. A method for determining an arousal level of a subject, the method comprising:
   (i) receiving a bio-signal from a wearable device worn by the subject, the bio-signal including at least one selected physiological parameter, the at least one selected physiological parameter including pulse pressure;
   (ii) segmenting the bio-signal into a plurality of processing windows, each processing window having a time duration that is adaptively configured depending on the at least one selected physiological parameter to include at least five consecutive cardiac cycles of the bio-signal;
   (iii) calculating statistical variation of the at least one selected physiological parameter including pulse pressure derived from the at least five consecutive cardiac signals of the bio-signal;
   (iv) determining the arousal level of the subject based on the calculated statistical variation of the at least one selected physiological parameter including pulse pressure, wherein the arousal level is determined to be in a stress level if the calculated statistical variation of the pulse pressure is greater than a threshold value, in which the threshold value is within a range of about 3.0-12.0 mmHg mercury level, and
   (v) outputting the arousal level and, based on the determined arousal level, a training or an intervention to assist with managing the stress level.

2. The method of claim 1, wherein the at least five cardiac cycle includes time intervals relating to a systolic peak, start time and end time of each cardiac cycle.

3. The method of claim 1, wherein calculating the statistical variation of the at least one selected physiological parameter including pulse pressure includes calculating a standard deviation of the pulse pressure.

4. The method of claim 3, wherein the arousal level is determined to be in the stress level if the calculated standard deviation of the pulse pressure is greater than the threshold value, in which the threshold value is within a range of about 6.0-10.0 mmHg mercury level.

5. The method of claim 1, wherein the at least one physiological selected parameter comprises first and second physiological parameters derived from the bio-signal, wherein one of the first and second physiological parameters is the pulse pressure, and the other of the first and second physiological parameters is selected from the group consisting of respiration rate and heart rate.

6. A computer program stored in a storage medium of a wearable device, the computer program having a set of instructions, when executed, is arranged to control a processor of the wearable device to perform the method of claim 1.

7. A wearable device for determining an arousal level of a subject, the wearable device including a processor configured to perform the method of claim 1.

8. A method for deriving a mental state of a subject, the method comprising:
   (i) receiving a bio-signal from a wearable device worn by the subject, the bio-signal including at least two selected physiological parameters, one of which includes pulse pressure;
   (ii) segmenting the bio-signal into a plurality of processing windows, each processing window having a time duration that is adaptively configured depending on the at least two selected physiological parameters to include at least five consecutive cardiac cycles of the bio-signal;
   (iii) calculating respective statistical variations of the at least two selected physiological parameters derived from the at least five consecutive cardiac cycles of the bio-signal;
   (iv) determining an arousal level of the subject based on the calculated statistical variations of the at least two selected physiological parameters, and
   (v) outputting the arousal level and, based on the determined arousal level, a training or an intervention to assist with managing the arousal level.

9. A method of claim 8, wherein the at least two selected physiological parameters further include one of respiration rate and heart rate.

10. A wearable device for deriving a mental state of a subject, the wearable device including a processor configured to perform the method of claim 8.

* * * * *